United States Patent
Ferguson et al.

(10) Patent No.: US 7,125,499 B2
(45) Date of Patent: Oct. 24, 2006

(54) LIQUID CRYSTAL POLYMER TECHNOLOGY CHEMICALS AND APPLICATIONS

(75) Inventors: Thomas David Ferguson, Cincinnati, OH (US); Rakesh Govind, Cincinnati, OH (US)

(73) Assignee: LCP Tech Holdings, LLC, Cincinnati, OH (US)

( * ) Notice: Subject to any disclaimer, the term of this patent is extended or adjusted under 35 U.S.C. 154(b) by 358 days.

(21) Appl. No.: 10/486,458

(22) PCT Filed: Aug. 12, 2002

(86) PCT No.: PCT/US02/25430

§ 371 (c)(1), (2), (4) Date: Feb. 10, 2004

(87) PCT Pub. No.: WO03/016433

PCT Pub. Date: Feb. 27, 2003

(65) Prior Publication Data

US 2005/0072960 A1    Apr. 7, 2005

Related U.S. Application Data

(60) Provisional application No. 60/311,383, filed on Aug. 13, 2001.

(51) Int. Cl.
*C09K 19/38* (2006.01)
*C09K 19/34* (2006.01)
*F01P 11/08* (2006.01)
*C01M 107/52* (2006.01)
*C08G 70/08* (2006.01)
*C08G 77/56* (2006.01)
*C08G 77/398* (2006.01)

(52) U.S. Cl. .......... 252/299.01; 252/299.61; 252/299.63; 123/41.33; 123/41.42; 508/155; 508/188; 508/190; 528/7; 528/13; 528/394

(58) Field of Classification Search .......... 252/299.01, 252/299.61, 299.63; 508/110, 155, 188, 508/190; 123/41.33, 41.42; 528/7, 13, 394
See application file for complete search history.

(56) References Cited

U.S. PATENT DOCUMENTS

| | | |
|---|---|---|
| 3,086,996 A | 4/1963 | Shapiro et al. |
| 3,101,369 A | 8/1963 | Brotherton et al. |
| 3,489,528 A | 1/1970 | Zanieski |
| 4,581,468 A | 4/1986 | Kazimiera et al. |
| 6,277,348 B1 | 8/2001 | Pujol et al. |

FOREIGN PATENT DOCUMENTS

| | | |
|---|---|---|
| EP | 0 104 412 A | 4/1984 |
| EP | 0 934 982 A1 | 8/1999 |
| WO | WO 88/02003 | 3/1988 |
| WO | WO 99/01378 | 1/1999 |

*Primary Examiner*—Shean C Wu
(74) *Attorney, Agent, or Firm*—Lafkas Patent LLC; David M. Lafkas

(57) ABSTRACT

Liquid phase liquid crystal polymers (LCPs) are disclosed having a composition and structure that can be varied to provide desirable properties. The liquid phase LCPs have polyiminoborane, polyaminoborane, and/or borozine polymer backbone molecules, with silicon and/or phosphorous side chain molecules linked to the backbone that provide a degree of alignment assigned an Order Parameter (S), defined as $S=\frac{1}{3}[3\cos^2\theta-1]$, where $\theta$ is the angle between the axis of an LCP molecule and the vertical direction. The inventive liquid phase LCPs have an average Order Parameter in the range of about 0.2 to about 0.99 and are applicable to a number of rinse, coolant, lubricant, sterilization and other protectant processes.

19 Claims, 3 Drawing Sheets

LIQUID CRYSTAL POLYMER TECHNOLOGY CHEMICALS AND APPLICATIONS

RELATED APPLICATIONS

This application claims priority to related U.S. application Ser. No. 60/311,383 filed Aug. 13, 2001 which is expressly incorporated by reference herein in its entirety.

This invention was made as part of co-inventor Ferguson's duties as an employee of the United States Government. The Government has certain rights in the invention.

BACKGROUND

The invention relates generally to liquid phase liquid crystal polymers having imino- and amino-borane backbone chains with side chains that impart desirable properties and applications.

DISCUSSION OF RELATED ART

Crystal polymers are long chain linear molecules that have a preferred orientation. Most crystal polymers are solids under ambient conditions; however, they are conventionally referred to as liquid crystal polymers because they have characteristics intermediate between solid and liquid phases. Such polymers have found extensive use in the electronic market sector, and are widely used in displays for products such as digital watches, television sets, etc.

Further structural and chemical modifications of these polymers would be useful to determine additional properties and applications.

SUMMARY

One class of crystal polymers are in a liquid phase, rather than a solid phase, and are termed liquid phase liquid crystal polymers (LCPs). The molecules in liquid phase LCPs are aligned to a degree that is less than the alignment of molecules in solid phase liquid crystal polymers, but greater than the randomly oriented molecules in liquids.

Compositions and structures of liquid phase liquid crystal polymers (LCPs) are varied to provide desirable properties. The inventive liquid phase LCPs have a polyiminoborane $[BNH_2]_x$, and/or polyaminoborane $[BNH_4]_x$ backbone, with various compositional and structural silicon and/or phosphorous side chain linkages to the backbone. For example, in one embodiment, the ratio of the length of the side chain to the length of the main chain is varied. The linkages provide a degree of alignment to the liquid phase LCP molecules that is quantified by an Order Parameter. The inventive liquid phase LCPs have an average Order Parameter (S) in the range of about 0.2 to about 0.99, such that they exist in a liquid, rather than a solid, phase. Thus, although isolated compounds may have an Order Parameter greater than 0.99, the average of the Order Parameters will be less than that of a solid phase composition, that is, less than 1.0.

The inventive liquid phase LCPs are applicable to a number of uses including, but not limited to, compositions and methods for rinsing, lubricating, cooling, and protecting from agents such as moisture, light, pests, bacteria, etc. In one embodiment, liquid phase LCPs having relatively lower Order Parameters within the 0.2 to 0.99 range are used for rinsing processes, and liquid phase LCPs having relatively higher Order Parameters within this range are used for surface protectant processes, e.g., surface sterilization. Liquid phase LCPs having any Order Parameter within this range may also be used for lubricant, coolant, and other protectant processes. Additionally, as will be appreciated by those skilled in the art, the Order Parameter values may overlap, and the compounds may be used for more than one application.

One embodiment of the invention is a composition and method using the inventive liquid phase LCPs for rinsing process chemicals, for example, rinsing acids or alkaline solutions from processed metal products, to approach a zero discharge for the rinse agent. In this embodiment, liquid phase LCPs are prepared that have a density/specific gravity that is sufficiently different from the process chemical to be removed, such that two distinct immiscible layers form, analogous to the separation of oil and water. The process chemical(s) being rinsed from the product can therefore be reclaimed in full strength and can be returned in an uncontaminated state to the original process. The LCPs can similarly be recovered from the rinsing process. This method reduces the volume of rinse water that is required, and can approach or achieve zero discharge of water from typical chemical processes.

Another embodiment of the invention is a composition and method using the inventive liquid phase LCPs as a lubricant and/or a coolant, including cutting fluids for machining, grinding, drilling, milling, stamping, etc. processes. The liquid phase LCPs may be used as a hydraulic fluid and/or an engine fluid.

Other embodiments of the invention are compositions and methods of the inventive liquid phase LCPs as environmentally safe protectants. They can, for example, be applied to inert surfaces to protect against bacteria (e.g., hospital surfaces), applied to vegetation to retain moisture and to retard fires (e.g., forest fires), applied to lumber and other construction material to protect against termites, mold, mildew, etc., applied to biological and non-biological surfaces to protect against damage by ultraviolet light, as well as numerous other uses.

These and other embodiments of the invention will be apparent in view of the following figures and detailed description.

DETAILED DESCRIPTION

The structure of a solid is generally well ordered, with the molecules closely packed and aligned in fixed positions to give a size and shape. The molecules of a liquid are also closely packed, but they are not bound to fixed positions. A liquid is fluid, and its structure is less ordered than that of a solid. A liquid also has a defined volume and is without a shape, being able to take the shape of its container.

Figure 1A:
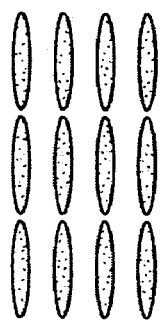
FIG. 1 schematically illustrates molecular alignments in solids (FIG. 1A), liquid phase liquid crystal polymers (LCPs) (FIG. 1B), and liquids (FIG. 1C).
Figure 1B:
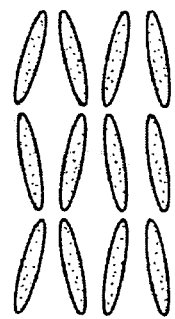
Figure 1C:
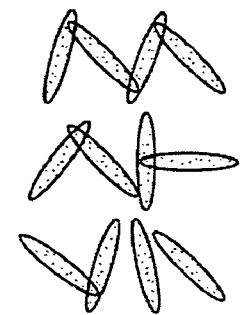

FIG. 1 schematically illustrates the molecular alignments in compositions that are solid (FIG. 1A), liquid (FIG. 1C), and liquid phase liquid crystal polymers (LCP) (FIG. 1B). In a solid, the molecules are ordered and are perfectly aligned, whereas in a liquid, the molecules are oriented or ordered randomly. In a liquid phase LCP, the molecules are aligned and hence are not randomly oriented, but their alignment is less than that of a solid.

The degree of alignment of the molecules in a liquid phase LCP can be quantified by an Order Parameter (S). S is defined as $\frac{1}{2}[3\cos^2\theta - 1]$, where $\theta$ is the angle between the axis of a liquid phase LCP molecule and the vertical direction. In a solid, the Order Parameter has a value of 1.0, because all the molecules are perfectly aligned. In a liquid, the Order Parameter has a value of 0 because all the molecules are randomly oriented. In a liquid phase LCP, the average Order Parameter varies in the range of between about 0.2 and about 0.99.

The value of the Order Parameter for a particular liquid phase LCP depends upon factors such as its chemistry, its molecular structure, the number and composition of the repeating units of the polymer, etc. The inventive liquid phase LCPs have an Order Parameter that is, on average, in the range of about 0.2 to about 0.99, such that they exist in a liquid, rather than a solid, phase. Thus, although isolated compounds may have an Order Parameter greater than 0.99, on average and with a standard deviation of ±0.01, the Order Parameter for any liquid phase LCP is less than that of a solid phase composition, that is, less than 1.0, when evaluated at ambient conditions (e.g., STP).

The structure has a polymer backbone chain of polyiminoborane —BH—NH—BH—NH—$[BNH_2]_x$, polyaminoborane —$BH_2$—$NH_2$—$BH_2$—$NH_2$ $[BNH_4]_x$, (abbreviated as B'polymers $[B_3N_3H_6]_x$ (abbreviated as BZ). The backbone chain is modified by side chain linkages using silicon (Si—N—B) and/or phosphorous (B—N—P). X (the backbone) is in the range of about 10 to about 90. With the side chains, the structures are (—BH—NR—BH—NR'—)$_x$ (abbreviated as PIB), (—$BH_2$—NHR—BH—NHR'—)$_x$ (abbreviated as PAB), and

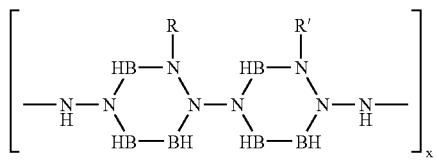

(abbreviated as PBZ), where R and R' are linear polydimethylsiloxane polymers $(CH_3)_3SiO[SiO(CH_3)_2]_nSi(CH_3)_3$, and n is in the range of about 1–130. The backbone polymers are commercially available (e.g., Sigma, St. Louis Mo.), and the side chains are added by emulsion polymerization at ambient temperature combining the dimethylsiloxane polymer and B—N and/or BZ, using phosphorous trichloride (1% by weight) as a catalyst. The emulsion polymerization reaction is conducted in water phase.

The side chain linkages alter the structure of the basic B—N and/or BZ polymer chain to modify its properties, as desired, by altering the value of the Order Parameter. By varying the numbers and types of linkages, any value of the Order Parameter can be achieved. Such structures and the resultant properties were determined using SPARTAN software, commercially available from Wavefunction, Inc. (Irvine Calif.). The SPARTAN software is used to analyze the structure of liquid phase LCPs and to calculate some properties. The structure and properties of liquid phase LCPs may also be evaluated by other analytical methods known to one skilled in the art, such as x-ray crystal diffraction, NMR, IR, etc.

The applications for structures providing different uses or properties are achieved by varying the length of the B—N or BZ polymer chain and/or by varying the types of linkages, as previously described to form PIB, PAB, and/or PBZ. The inventive liquid phase LCPs thus can be applied to varied and unique process by varying values of the Order Parameter. The inventive compounds have a variety of desirable properties. They are non-toxic, physiologically inert, water insoluble, and not susceptible to attack or biodegradation by organisms such as bacteria, fungi, termites, etc. Once the liquid phase LCP is applied to a surface, it "cures" to a solid phase.

Evaluation of biodegradability was by the Manometric Respirometry Method (Organization for Economic Cooperation and Development (OECD)) 301F, using a standard respirometer. The method uses a closed system to evaluate biodegradation by measuring the amount of oxygen consumed by microorganisms due to aerobic biological degradation of the test material, in this case the liquid phase LCPs. Evolved carbon dioxide is removed and consumed oxygen is replaced. The method requires use of microorganisms not acclimated to the test material; that is, microorganisms which were not previously exposed to the inventive liquid phase LCPs. The method also requires that the microorganisms include a minimum concentration of 75% domestic influent; speaking to its ability to evaluate municipal treatment systems (POTWs) for biodegrade materials which may be used in, and subsequently disposed of, from homes, schools, office buildings, etc.

As a guideline, a "readily biodegradable" material is one in which $\geq 60\%$ of the material is degraded within 28 days. This indicates that the material has a propensity to biodegrade rapidly and completely in a range of natural aerobic environments. An "inherently biodegradable" material is one in which >20% of the material is degraded within 28 days. This indicates the material has a potential for biodegradation.

Liquid phase LCPs (B—N and BZ) were added directly to the aqueous medium containing microorganisms with continuous stirring. Data were collected over a 28-day period, and each sample was tested in triplicate. The liquid phase LCPs did not exhibit any oxygen uptake in aqueous system over the 28-day evaluation period. In comparison, control materials that did not contain liquid phase LCPs did exhibit oxygen uptake, as shown in the following table.

| Oxygen Uptake Using Method 501F (OECD) | | |
|---|---|---|
| Time (days) | Average Oxygen Uptake (mg/L) using B-N or BZ | Average Oxygen Uptake in Control Flasks (mg/L) |
| 0 | 0 | 0 |
| 2 | 0 | 2.6 |
| 4 | 1.2 | 4.3 |
| 6 | 1.0 | 6.8 |
| 8 | 0.4 | 10.8 |
| 10 | 0.3 | 14.9 |
| 12 | 0.6 | 16.3 |
| 20 | 0.4 | 22.5 |
| 28 | 0.8 | 30.7 |

The liquid phase LCPs were non-toxic to the microorganisms used in the test system, and were not degraded by these organisms. Physiological inertness was evaluated by the OECD method, previously described, and showed no bacterial attack using activated sludge organisms.

A modified ASTM E686 (Standard Method for Evaluating Anti-Microbial Agents in Aqueous Metal Removal Fluids) test procedure were performed. A sample of biologically deteriorated metal removal fluid was obtained and its bacterial level was determined using a dip-slide. The bacterial count was not less and $10^7$ bacteria/ml. Dilute metal removal fluid (600 ml) was poured into a one-liter wide mouth clear glass jar. Ten grams of aluminum machining chip, and 60 ml of a rancid metal removal fluid were added. The cap was screwed on and the sealed jar was inverted a number of times for complete mixing. The fluid was evaluated for bacteria level and odor generation.

The samples were placed in a constant temperature environment (90° F. ±5° F.) and the fluid was aerated for five days using a fish tank air pump, plastic or rubber tube, and fish tank aeration stone placed as close to the bottom of the uncapped fluid container as possible. Aeration was stopped after five days, and the sample was evaluated for bacterial level and odor generation. Aeration was suspended for about 2.5 days and the sample was again evaluated for bacterial level and odor generation. Two additional cycles (five day aeration, 2.5 day no aeration) were repeated with appropriate measurements. The following results were obtained.

Day 0 liquid phase LCP (clear, odorless); no bacteria present
  aluminum chip and contaminated fluid added; $10^8$ bacteria/ml and rancid smell
  mixing; thick brownish fluid with rancid smell
  aeration on
Day 5 $10^3$ bacteria/ml (lower limit dip slide)
  aeration off
Day 8 fluid separated into two distinct layers; no bacteria detected and rancid smell
  aeration on
Day 12 fluid one continuous brown layer; $10^3$ bacteria/ml (lower limit dip slide), rancid smell
  aeration off
Day 15 fluid separated into two distinct layers; no bacteria and rancid smell
  aeration on
Day 19 fluid one continuous brown layer, $10^3$ bacteria/ml (lower limit dip slide), rancid smell
  aeration off
Day 22 fluid separated into two distinct layers; no bacteria and rancid smell These data indicated that the liquid phase LCPs are physiologically inert. When mixed with the biologically deteriorated contaminant fluid, they did not support bacterial growth. When a well mixed solution of contaminated oil was mixed with the liquid phase LCPs, such as during aeration, the dip-slides showed low-level quantities of bacteria present in the mixture. However, when the mixture was undisturbed and the oil and liquid phase LCPs separated into layers, bacteria were present only in the oil layer and not in the LCP layer. These results indicated that liquid phase LCPs are not adsorbed by living organisms, rendering them applicable for biological uses such as in the medical and food-industries.

Liquid phase LCPs are inflammable and have a high boiling point (greater than about 550° F. according to ASTM methods). When subjected to a temperature of 875° F., the liquid phase LCP began to boil, then evaporated to a solid phase.

Liquid phase LCPs are stable in the presence of oxidizing agents. They are not reactive with acids (e.g., chromic acid), alkali, electroplating solutions such as acid and alkaline zinc solutions, nitric acid, etc. Liquid phase LCPs that are mixed with chromic acid, for example in electroplating systems, form a protective cover over the chromic acid. When mixed and heated to temperatures up to 200° F., a liquid phase LCP was stable for more than two years with chromic acid, and more than one and one-half years with a commercial oxidizing agent having a pH<2 Picklex®, an acid zinc solution for electroplating, an alkaline zinc solution for electroplating, and nitric acid.

Liquid phase LCPs have a very low vapor pressure at ambient and near ambient temperatures. Evaporative losses of the inventive liquid phase LCPs were monitored using standard ASTM vapor pressure testing methods. At temperatures of 150° F., the vapor pressure of a liquid phase LCP was less than 0.5 mm Hg.

Liquid phase LCPs are transparent upon visual inspection. They are immiscible with water and aqueous mixtures; and are less dense than water so that they float as a separate layer in aqueous systems.

Liquid phase LCPs lubricate a surface to which they are applied, rendering the surface slippery. Therefore, parts coated with liquid phase LCPs should be handled with care and using precautionary measures, such as gripping devices, ribbed gloves, etc. Surfaces on which liquid phase LCPs have been spilled should be wiped to reduce a danger of slippage (floors, etc.). Liquid phase LCPs cause nylon parts to swell, thus liquid phase LCPs coatings applied to nylon seals, etc., may weaken these structures.

Various applications of the above compositions are disclosed.

Rinse Applications

In many production processes, a chemical that has been used in a process must be removed from the resulting product. Typically, such washing or rinsing utilizes water, frequently in copious amounts, that then becomes polluted and/or contaminated with the process chemical that is being removed. Water, a valuable resource, is therefore consumed in the rinse process. Moreover, the polluted and/or contaminated rinse water causes environmental concerns or problems.

The inventive liquid phase LCPs address these problems by both minimizing the use of water and, further, by allowing the process chemical to be reclaimed. Liquid phase LCPs can be used to rinse chemicals and/or contaminants from products using reduced volumes of water and/or other solvents. They may be prepared in the form of a bath, a spray, etc. and may be dipped, brushed, rolled, misted, coated, or otherwise applied to accomplish a rinsing function.

In one embodiment, liquid phase LCPs for rinse processes are prepared to result in an Order Parameter in the range between about 0.2 to about 0.99. In another embodiment, liquid phase LCPs for rinse processes are prepared to result in an Order Parameter in the range between about 0.5 to about 0.8. Compositions that result in these Order Parameters include the chemical structure previously described where n is in the range of 20–100.

The inventive liquid phase LCPs are benign to the chemical or the contaminant that is being removed from the product. The liquid phase LCPs have a density/specific gravity that is sufficiently different from the process chemical to be removed, such that two distinct immiscible layers form. The process chemical(s) rinsed from the product can therefore be reclaimed in full strength, and can be returned to the original process in an uncontaminated state. The LCPs can similarly be recovered from the rinsing process, e.g., by decanting. This method significantly reduces the volume of water needed for rinsing, and can approach or achieve zero discharge of water from typical chemical processes.

Among the numerous industries in which the inventive liquid phase LCPs may be used, the metal finishing industry is described for illustrative purposes only, but the invention is not so limited. In metal finishing processes, several rinse tanks are often necessary to remove the process chemical. The process chemical that must be rinsed from a metal product may be a cleaner, a degreaser, or other process chemical or undesired contaminant/solution, such as chromic acid that is frequently contained in an electroplating tank. The liquid phase LCP rinse is benign to the chemical solution, chromic acid in this example, to be rinsed off of the product. The chemical solution easily separates from the liquid phase LCP rinsing agent, forming two layers. A final rinse with water may be used, from which the liquid phase LCP rinsing agent can also be easily recovered. For a final product that will require lubrication, no rinsing is needed because the liquid phase LCP also provides a lubricant function.

In a typical process, a product or part is treated in a bath containing one or more chemicals, then is rinsed in one or more rinse tanks containing water. After the rinse tanks are contaminated by the chemical, the water eventually has to be replaced. In the inventive process, the parts are rinsed in a liquid phase LCP that is environmentally benign. The rinsing can be accelerated by agitation and, in some cases, by heat. The operating temperature for rinsing can be the same as the chemical bath which, in many electroplating processes, ranges from about 65° F. to about 190° F. Lowering or raising the temperature of the rinse bath may be desired based on the individual chemical process, rinse time desired for production, energy costs, and/or other factors.

Figure 2:
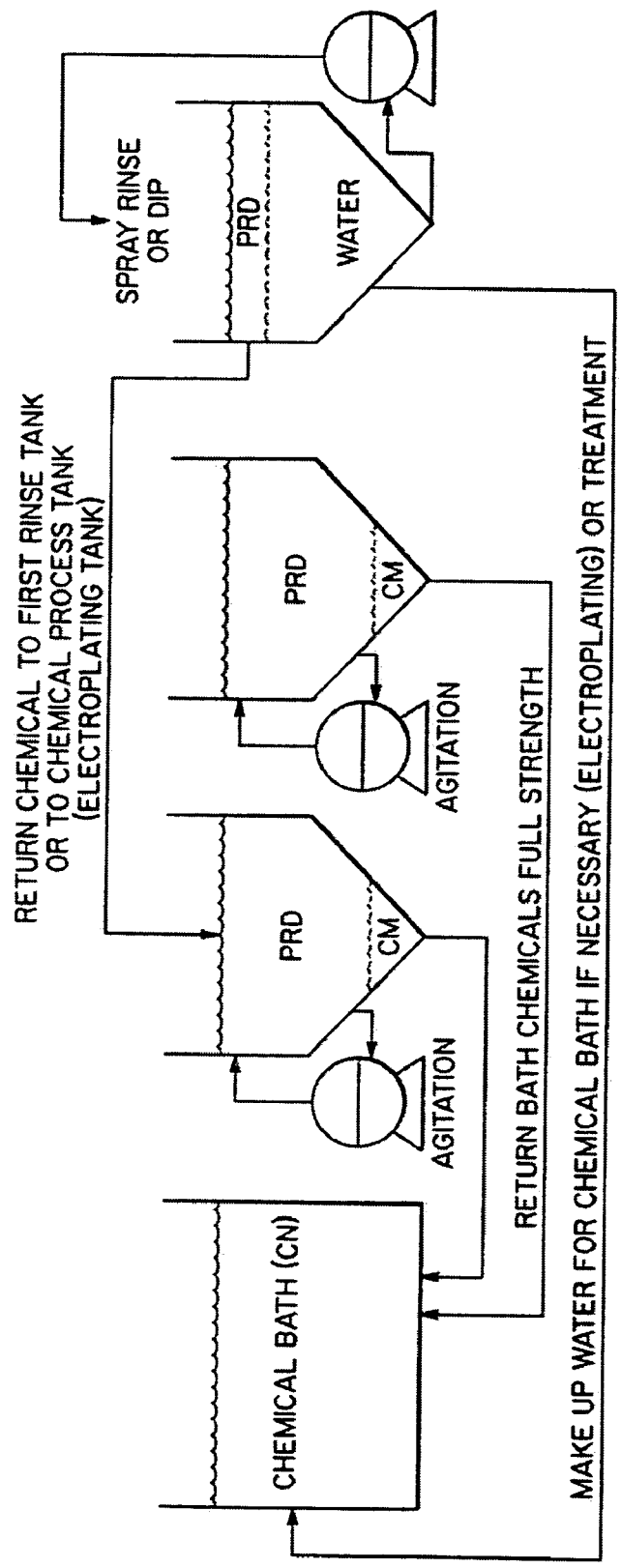
FIG. 2 illustrates one configuration of a rinsing application for the inventive liquid phase LCPs.

FIG. 2 illustrates one of many possible tank configurations for the inventive rinsing process. The tanks may be positioned directly next to each other to avoid spills or drips of chromic acid or other process chemicals. The part is treated in the chemical bath and then is rinsed in the first rinse tank, which contains the inventive liquid phase LCP. The first rinse tank may be agitated to facilitate rinsing and, depending upon the chemical in the first bath, may advantageously be heated. In the first rinse tank the process chemical (CM) separates from the liquid phase LCP and sinks to the bottom of the tank, similar to the separation of oil and water. If periodic removal of the process chemical is desired or necessary, agitation may be stopped and separation will occur within a few minutes, then the process chemical may be drained, pumped, or otherwise transferred back into the first tank. It may also be filtered to remove dust or suspended metal particles. A similar process occurs with a second rinse tank, if a second rinse tank is necessary. Optimum agitation with proper baffles to promote separation of the process chemical and liquid phase LCP desirably decrease production time in the rinse phase. The next rinse tank uses water to separate the liquid phase LCP, which can be skimmed off the top or otherwise removed from the tank and placed back in the first rinse tank. The rinse water in the third tank, which will eventually be contaminated with trace amounts of process chemical from the first tank, can be used in the bath to make up for water losses in processes that require water, such as most electroplating processes where water loss occurs from electroplating baths due to evaporation and conversion to hydrogen and oxygen gases from electrolysis of water during the plating operation. This desirably creates a zero discharge process for water. Alternatively, the water can be treated (if necessary) and discharged. Because the inventive liquid phase LCPs are environmentally benign, a water rinse may not be necessary if the product does not require further processing. In this case, simply spraying, dipping, and/or otherwise contacting the part to be processed with the liquid phase LCP will suffice.

In another embodiment of the above process, the rinsing application may be incorporated into other applications, such as the use of liquid phase LCPs as fume suppressants, etc. The LCP is added for one application, and then may be returned to the process tank for subsequent rinsing of the part.

The inventive liquid phase LCPs do not interfere with the chemical process. If rinsing is the final process, interference is not a concern, but if rinsing is an intermediate process, interference with one or more chemical processes may be an issue. In the embodiment described above, possible interference of a liquid phase LCP having the structure previously described, where n=70, was evaluated by using it in a chrome electroplating bath. There were no adverse effects, however, from the liquid phase LCP in hard chromium plating baths. The liquid phase LCP was environmentally benign and did not mix with chromic acid, nor with PICK-LEX®, which is an organic acid with a pH<2, nor with highly alkaline solutions. Based on these data, liquid phase LCPs were predicted to be benign with respect to most chemical processes. Examples of chemical processes in which liquid phase LCPs for rinsing applications can be used include, but are not limited to, hexavalent chromium plating, nickel plating, nickel strikes, copper plating, cadmium plating, zinc plating, trivalent chromium plating, electroless nickel and copper, sulfuric acid anodizing baths, sulfuric or hydrochloric acid pickling baths and strip solutions, sulfuric or nitric acid pickling, etching, brightening baths for copper or brass, nitric/hydrofluoric acid pickling baths and strip solutions, phosphoric and/or sulfuric acid baths, etch solutions, methane sulfonic acid (MSA) solutions, cyanide solutions, chromic acid-based solutions, chromic acid anodizing solutions, etchants and chromating solutions, organic finishes, zinc solutions, tin and tin/lead solutions, and other non-metal finishing processes.

EXAMPLE 1

In a bench scale test of both conventional rinsing systems and the inventive rinsing methods, an electroless nickel solution was used as the process chemical. The solution contained high levels of nickel, as well as various other chemicals used as brighteners.

In the conventional rinsing system, a concern is the amount of nickel that must be treated and discharged. The first rinse tank using the conventional system had a nickel level of 1800 mg/l. The inventive process, using the structure previously described where n=70, was able to return all the nickel plating bath back to the original process tank, which involved no contamination of any rinse water. The second rinse tank using the conventional system had a nickel level of 265 mg/l. The second rinse tank in the inventive process was the final water rinse that rinsed off the liquid phase LCP for recovery, and had a nickel level of 63 mg/l. A third rinse tank was required using the conventional system to reduce the nickel levels down to 16 mg/l. The conventional system also did not recover the chemical bath, and contaminated a significantly greater amount of water, compared to the inventive rinsing method.

EXAMPLE 2

A right-angled bent piece of metal sheet was dipped in an electroless nickel solution, then in a liquid phase LCP solution using the structure previously described where n=35. This liquid phase LCP had a lower viscosity than the one used in Example 1. Dipping was repeated over 200 times. This allowed sufficient chemical solution to be carried into the liquid phase LCP rinse liquid container, and sufficient liquid phase LCP rinse liquid as well as the chemical solution to be carried into the water rinse container.

The chemical solution that was carried into the liquid phase LCP rinse liquid container formed a separate layer at the bottom of the container. The liquid phase LCP that was carried into the water rinse container floated as a separate layer on top of the water surface.

Lubricant/Coolant Applications

A workpiece or part that is being manufactured typically requires a final finish for permanent corrosion protection. Products that contain oil are used for finishing, as well as for lubricating and cooling. Such products make it difficult for machining and stamping operations to meet regulatory levels of effluent oil and grease. Metal finishers in subsequent operations, which provide final finishes to the part, also have to deal with the oils that are left on the part. These oils can adversely affect the final finish by causing problems with adhesion of the final coat. The traditional cutting and stamping oils that are used are removed by strong alkaline cleaners or solvents, which add significantly to the pollution generated from these operations. The cutting and stamping oils also are a source of pollution.

The inventive liquid phase LCP structures and applications are used for processes in which a lubricant and/or coolant is required or is desirable. Applications include, but are not limited to, cutting fluids for machining, grinding, drilling, milling and stamping, uses as hydraulic and/or engine fluids, and coolants. Liquid phase LCPs as metal removal fluids, cutting fluids, and/or stamping fluids significantly reduce the pollution generated from these processes. Additionally, unlike oils and cutting fluids, the liquid phase LCPs can be easily removed and reused.

Liquid phase LCPs can be formulated for lubricant/cooling applications in any way that will result in an Order Parameter in the range of about 0.2 to about 0.99. For lubricant/cooling applications, a wide variety of angles may occur. As a cutting fluid, the long thin molecules are lined up end to end with an angle in the range of about 10° to about 15°. With hydraulic fluids under pressures greater than 2000 psi, the long thin chains are compressed, which may cause increased wear on the hydraulic system. A smaller angle, less than about 5°, is more suitable for hydraulic fluids, and this angle can be achieved by preparing liquid phase LCPs with the structure previously shown with smaller side chains, in one embodiment, where n is in the range between 1 and 10.

The liquid phase LCPs lubricated and cooled the metal chip/tool/workpiece interface. This allowed for extended tool life, operation at higher machine tool speeds and feeds, enhanced part quality, and flushing of metal chips or swarf away from the cut zone. It also provided temporary corrosion protection. Additionally, unlike traditionally used oils, liquid phase LCPs are easily removed from a part and are recaptured and reused. Simply rinsing the parts in water, prior to the final processing of the finish coat, allowed the liquid phase LCPs to float to the top of the tank and be easily removed and reused.

Other ways of removing the liquid phase LCPs which will provide longer term corrosion resistance to the part may also be used. One possibility is the use of PICKLEX®, whereby the parts are simply placed into a PICKLEX® bath for about one minute, after which the liquid phase LCP floats to the top of the bath and is removed for reuse using any removal methods desired, such as draining, skimming, etc. The parts, now protected, are ready for a final finish without any residual oil and grease that often cause final finishes to fail. Additionally, parts to be forwarded for metal finishing are oil and grease free, which eliminates a significant pollution problem for metal finishing shops.

EXAMPLE 3

A liquid phase LCP, having the structure previously shown where n=70, was evaluated for use as a motor oil, comparing engine performance to a standard motor oil in both a truck and a lawnmower engine.

The engine of a 24 year old diesel truck, worn but in good operating condition, was evaluated. The engine temperature and oil pressure were taken every minute for 30 minutes, with the throttle locked in position at 1500 rpm at the beginning of each test. With the standard motor oil, the truck belched out a significant amount of black smoke. The next day, after the engine had cooled, the liquid phase LCP was added. The truck no longer belched out black smoke. The smoke was white with a very light blue-gray cast to it, much like a newer diesel engine. These observations suggested that the liquid phase LCP did not "burn" at normal engine temperatures, nor did it cause environmental detriment in relation to air emissions. The engine temperature took four minutes longer to reach the normal operating temperature of 185° F. This suggested that friction was reduced, causing a slower heat up, but the outside temperature was also about 5–10° F. cooler. The rpm increased to 1600 rpm when using the liquid phase LCP and had to be backed down to 1500 rpm, suggesting that increased lubricity of the liquid phase LCP allowed the engine to run faster. At 1500 rpm the oil pressure dropped from 50 psi to 38 psi as the engine heated. With the liquid phase LCP, the oil pressure dropped from 50 psi to 44 psi. This indicated that the viscosity of the liquid phase LCP did not break down as easily as that of standard motor oil.

In comparison tests of a lawnmower engine, the engine with liquid phase LCP ran 5° F. cooler than the engine with SAE 30 motor oil. The engine with liquid phase LCP also ran 30 minutes longer than the engine with SAE 30 motor oil on a full tank of gasoline under no load conditions. These results suggested that friction losses were reduced, and thus gas mileage was increased.

Liquid phase LCPs can be formulated to render the fluid more or less viscous, as desired, by varying the value of n in the polymer structure. Viscosity, the internal resistance to flow exhibited by a fluid, of the resulting structure may be predicted using the software program previously described, where a liquid phase LCP with a higher value of n has a higher viscosity than a liquid phase LCP with a lower value of n (e.g., a compound having the structure previously described where n=70 is more viscous than a compound having the structure previously described where n=35). Viscosity may also be determined using experimental methods, such as a viscometer, as known to one skilled in the art.

Different viscosities allow the compounds to have desired properties for various machining, milling, stamping, etc. operations, as well as for various lubricant, coolant, and hydraulic fluid applications.

The current practice of machining usually involves a machine with hydraulic fluid and lubricating fluid for the gear box or other parts on the machine. These fluids often contaminate the synthetic or other cutting fluids used in the machining process. The liquid crystal LCPs can be used just as a cutting fluid, or for extra benefit they can also be used to lubricate the machine, which solves the incompatibility problems with the various fluids. Also, a common problem with cutting fluids is growth of bacteria, whereas the inventive liquid phase LCPs do not support bacterial growth and are not consumed by living organisms.

EXAMPLE 4

Liquid phase LCPs are environmentally safe alternatives to petroleum based cutting oils, cutting fluids, and hydraulic oils. International Working Industry Group (IWIG) milling tests performed on a liquid phase LCP having the structure previously described where n=70 demonstrated superior performance while milling steel. It reduced both the resultant machining force, measured in pounds, in comparison to a baseline fluid and a typical cutting oil.

Figure 3A:
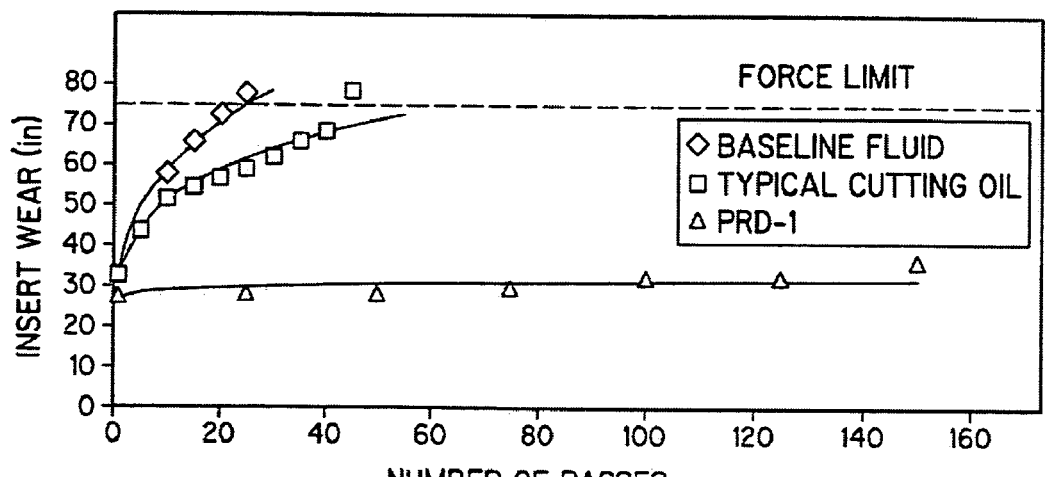
FIGS. 3A and 3B are graphs demonstrating, respectively, force measurements and insert wear measurements of a lubricating/cooling application for the inventive liquid phase LCPs.
Figure 3B:
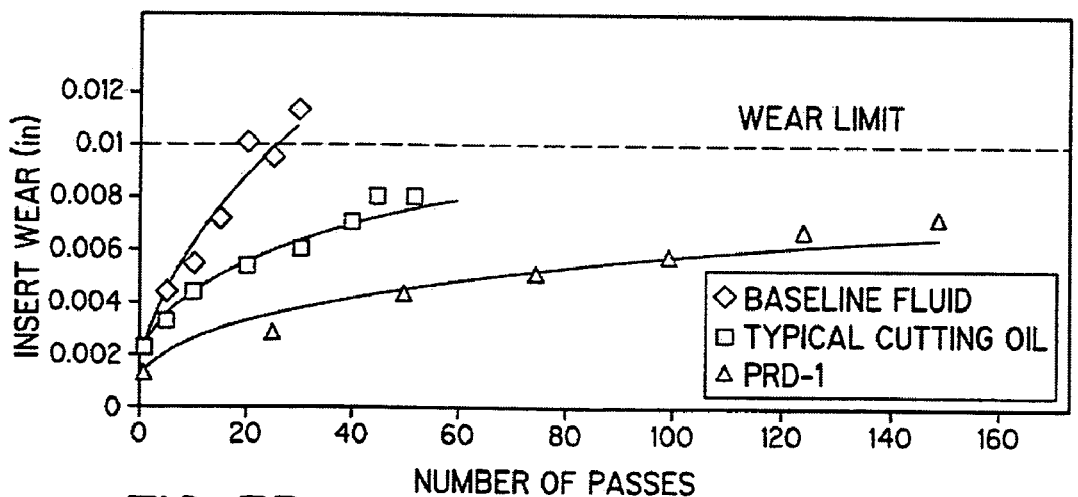

FIG. 3A provides comparative data for resultant machining force in pounds of a machine tool lubricated with a baseline fluid, a typical cutting oil, and the above-described liquid phase LCP. (identified as PRD-1). The machining force for a machine tool lubricated with baseline fluid began at about 32 pounds, but then increased after about thirty passes to over 80 pounds, which exceeded the limit of force of about 75 pounds. The machining force for a machine tool lubricated with a typical cutting fluid began at about 32 pounds, but then increased after about forty passes to almost 70 pounds. In contrast, the machining force for a machine tool lubricated with the liquid phase LCP began at about 28 pounds and maintained this force over about one hundred and fifty passes. FIG. 3B provides comparative data for insert wear, measured in inches, of the machine tool lubricated with the fluids described in FIG. 3A. The insert wear of the machine tool lubricated with a baseline fluid exceeded the wear limit of 0.01 inch after about 25 passes. The insert wear of the machine tool lubricated with a typical cutting oil showed 0.008 inch wear after about 60 passes. In contrast, the insert wear of the machine tool lubricated with the liquid phase LCP showed 0.006 inch wear after about 150 passes.

Theses data demonstrated that liquid phase LCPs offered about three times the insert life of the typical cutting oil under the test conditions; that is, they extended the life of the machine tool by about three times. The low machining forces demonstrated by the inserts which were cooled and lubricated with the liquid phase LCP indicated the performance difference between the typical cutting oil and a liquid phase LCP may be even greater.

Test data also indicated that the liquid phase LCP did not support the growth of bacteria that was found in the mixture of biologically deteriorated contaminant fluid and the liquid phase LCP, but did not kill the bacteria, as will be subsequently described for protectant applications. When the two components were well mixed, such as during aeration, dip-slide tests showed the presence of low-level quantities of bacteria in the mixture. When the two components had separated into different layers, dip-slide tests showed no bacteria in the liquid phase LCP layer.

EXAMPLE 5

Figure 5:
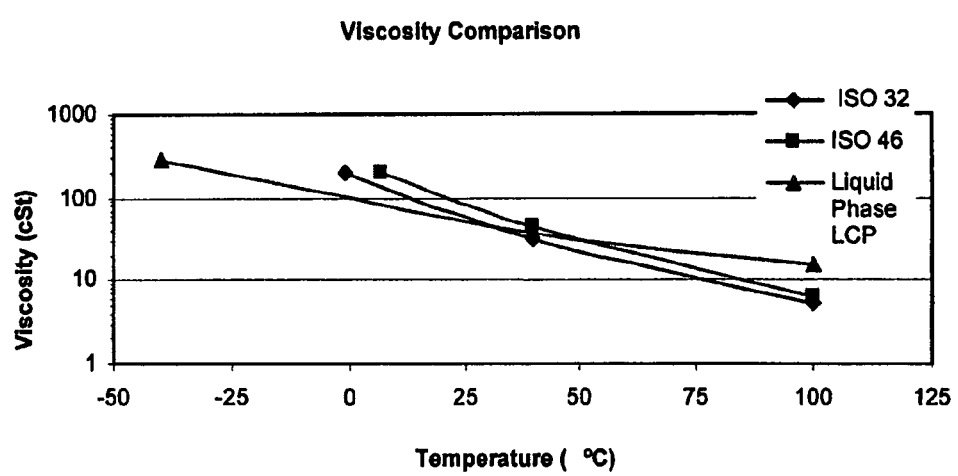
FIG. 5 is a graph of viscosity at various temperatures for a liquid phase LCP and mineral oil-based hydraulic fluids.

Viscosity testing of the inventive liquid phase LCPs was performed at −40° F. Testing was performed using ASTM Methods D-2161 and D-450, comparing viscosity of a liquid phase LCP having the structure previously described were n=70, to mineral oil-based typical ISO 32 and ISO 46 grade hydraulic fluids. The results are shown in FIG. 5, where viscosity (cst) is plotted against temperature (° C.).

The liquid phase LCP (triangles) had a better viscosity-temperature relationship in comparison to the two mineral oil-based fluids (squares ISO 46; diamonds ISO 32). This indicated that liquid phase LCPs provide thicker lubricant films, and thus more lubrication at higher temperatures, than counterpart mineral oil-based products. The liquid phase LCP had a flatter curve, which further indicated that the viscosity did not change as drastically as other fluids. The inventive liquid phase LCPs are thus likely suitable for speciality coolant/lubricants in extreme environments, such as in a spacecraft where one side of the craft is exposed to bitter cold while the other side is exposed to extreme heat from sun exposure. Other processes include use in aircrafts due to cold temperatures experienced at high altitudes, and any machinery or industrial processes in extreme temperature environments, either hot or cold.

Protectant Applications

Surface Sterilization Processes

Sterilization is a level of decontamination representing the complete elimination or destruction of all forms of microbial life, including fungal and bacterial spores. Conventional methods for surface sterilization involve the use of chemical agents which are sprayed on or otherwise applied to a surface. These agents typically contain biocides, which kill active organisms such as viruses, bacteria, fungi, etc. There are various problems with the use of these chemical agents. One problem is that sterilization is only temporary, and periodic spraying of the chemical agent is required to maintain its effectiveness against biological contamination. Another problem is the high cost of the chemical agent. Another problem is eventual cell-resistance to the agent, necessitating the use of new agents to which the organism population is not acclimated. Still another problem is the detrimental effect of chemical agents on the environment and, to some extent, on human health.

Figure 4:
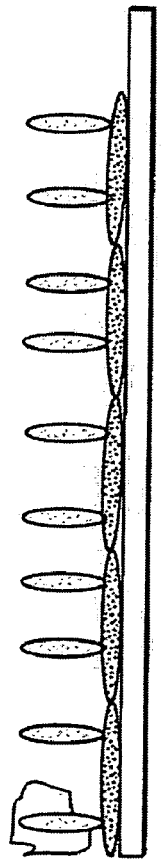
FIG. 4 schematically illustrates a possible mechanism for the inventive liquid phase LCPs as a protectant against microorganisms.

Liquid phase LCPs protect a surface from contamination by bacteria or other microorganisms. A possible mechanism for action of the liquid phase LCPs is that the side chain linkages, when polymerized on a surface, physically destroy the organisms. This may be by creating, in effect, molecular "needles", as schematically illustrated in FIG. 4, where the irregular shaped structure depicts a cell pierced by such a "needle". Active cells, spores, and viruses were unable to exist on an LCP-treated surface, possibly because the cell walls or membranes were pierced by these molecular "needles", thereby interfering with cellular process and imparting a sterilization effect.

For surface sterilization processes, the liquid phase LCPs have an Order Parameter that, on average, closely approaches 1. In one embodiment, liquid phase LCPs were prepared that resulted in an average Order Parameter in the range between about 0.2 to about 0.99. In another embodiment, liquid phase LCPs were prepared that resulted in an average Order Parameter in the range between about 0.97 to about 0.99. In another embodiment, liquid phase LCPs were prepared that resulted in an average Order Parameter of about 0.98. In still another embodiment, liquid phase LCPs were prepared that resulted in an average Order Parameter $\geq 0.97$. Compositions that resulted in these Order Parameters are those of the structure previously described where n is at least 100. In one embodiment, n is in the range between 100 to 130.

EXAMPLE 6

Wooden and polyvinylchloride (PVC) surfaces were coated, using a low pressure liquid sprayer, with a thin coating of a liquid phase LCP having the structure previously described with borane polymeric side chains of 10 units length. After the surfaces were incubated in controlled temperature chambers for about two weeks, standard cell counts were performed to quantitate the growth of microorganisms. Cell counts at the surface were generally less than one log cycle. Moreover, swabs taken from the coated surfaces and subsequently cultured did not show any growth, indicating that the cells present on the surface had been physically destroyed or damaged to prevent further growth. Control studies using the same wooden and PVC surfaces, not coated with the liquid phase LCPs, showed growth of a variety of viruses, fungi, and bacterial populations.

EXAMPLE 7

Liquid phase LCPs, having the structure and composition as described for surface sterilization processes, may be applied to a tooth surface. Such treatment may protect the tooth from permeation by bacterial by-products, for example, by hindering, slowing, or reducing the extent of permeation. Such by-products may otherwise causes harmful effects (e.g., caries, cavities), particularly in the low acidity environment of the oral cavity of adults, who have diminished natural protectant mechanisms. The liquid phase LCPs may be brushed on the tooth, and may be formulated as part of a dentifrice, such as a toothpaste. Alternatively, the liquid phase LCPs may be formulated as part of an oral rinse agent, such as a mouthwash or a fluoride treatment, for contact with the tooth. Other alternatives include formulations in strips, gels, powders, floss, etc. containing the inventive liquid phase LCPs.

Protection from Dehydration

Liquid phase LCPs are used for the treatment of vegetation, including plants, trees, crops, etc., to seal in moisture and to protect against wilting. This may be useful, for example, during times when the vegetation is exposed to dry conditions or to fire, or when watering is not possible.

In one embodiment, liquid phase LCPs as a protectant against dehydration were prepared to result in an Order Parameter in the range between about 0.2 to about 0.99, that is, polyiminoborane (PIB)$[BNH_2]_n$, polyaminoborane (PAB)$[BNH]_n$ and/or borozine polymers $[B_3N_3H_6]_n$, were modified to provide an Order Parameter in the range between 0.2 to 0.99. Compositions that resulted in these Order Parameters are those of the structure previously described where n is in the range between about 5 to about 100.

EXAMPLE 8

Dried wood pieces were sprayed with a liquid phase LCP having the structure previously described where n=70, using a hand-held sprayer. The amount of formulation sprayed was less than 1 liter of formulation/kg dried wood sprayed over a 100 square foot area. This ensured that the thickness of the liquid formulation was small on the surface and that the amount sprayed penetrated the porous wood and wood bark to some extent. As a control, equal amounts of dried wood pieces were assembled over a 100 foot area, but no formulation was sprayed.

The test and control areas of the dried wood pieces were lit with an open flame. The control area immediately caught fire, and the fire spread to all the dried wood pieces in the 100 square foot area. However, in the test area, the dried wood did not catch fire at all, even after repeated attempts to light the wood pieces with an open flame.

EXAMPLE 9

A liquid phase LCP, having the structure previously described where n=70, was sprayed on living outdoor plants (roses) outside a home using a hand-held sprayer. Two identical species of rose plants, each about three feet tall, were evaluated. One rose plant served as the test plant and was sprayed with the liquid formulation. The other rose plant served as the control plant and was not sprayed with the liquid formulation or any other liquid. Upon spraying, the formulation formed a thin film on the surface of the leaves and stems, and was partially absorbed in the leaves and stem through the pores. The formulation was sprayed every other day, to ensure that any new leaves emerging were also treated.

After about three weeks, the control rose plant was attacked by insects. This was evidenced by small holes riddling the leaves of the rose plant. During this same time period, however, the test rose plant was not attacked by insects at all, evidenced by healthy leaves without any holes. The treated plant continued to grow and maintain its health.

There was also a marked difference in growth between the treated and control rose plants; the control rose plant did not grow to the same extent as the treated rose plant. After three weeks, the treated rose plant had about three fully grown rose flowers, while the control plant did not flower at all, possibly due to attack by the insects. The treated rose plant was about six inches taller than the control rose plant, and also displayed larger leaves and longer stems than the control rose plant.

Because the inventive LCPs are not classified as insecticides, herbicides, or fertilizers, the mechanism by which insect and pest attack is reduced may be due to the liquid phase LCP coating the exposed plant parts (e.g., leaves, stems, flowers, etc.). A liquid phase LCP coating of these exposed structures permits greater retention of water. In turn, this facilitates unhindered normal plant functions, such as growth and the exchange of oxygen and carbon dioxide from the leaves. A surface coat of the inventive liquid phase LCPs on the exposed plant structures, protects them from insect and pest attack, whereas untreated plants lack this protection and hence may be more susceptible to attack.

Protection from Micro- and Microorganisms

The inventive liquid phase LCPs are used for the treatment of inert surfaces, such as wood, and/or for the treatment of biological surfaces, such as vegetation, to prevent damage by pests and disease.

In one embodiment, liquid phase LCPs are used for the treatment of a variety of inert porous and non-porous surfaces. In this embodiment, the alignment angle of the molecules in the liquid phase LCPs can vary in the range between about 5° to 25°. Liquid phase LCPs were thus prepared to result in an Order Parameter in the range between about 0.2 to about 0.99, that is, polyiminoborane (PIB)$[BNH_2]_n$, polyaminoborane (PAB)$[BNH_4]_n$, and/or borozine polymers $[B_3N_3H_6]_n$ were modified to provide an Order Parameter in the range between 0.2 to 0.99. Compositions that resulted in these Order Parameters are those of the structure previously described where n is in the range between about 5 and about 100.

Liquid phase LCPs may be applied to inert surfaces as a protectant from conditions that typically affect such surfaces. Surfaces include those associated with the construction industry, such as lumber, drywall, fiberglass, concrete, etc., those associated with the transportation industry, such as vehicle interiors, airplane interiors, railway interiors, etc., and those associated with and found in residential, commercial, hospital, food service, and/or other industrial settings. Examples of such surfaces are those found in bathrooms, kitchens, waiting rooms, and further include, but are not limited to, doorknobs, tables, counters, processing surfaces, appliances, bedding, furniture, window treatments, etc. Conditions include attack by bacteria, molds, mildew, fungi, viruses, and pests, and susceptibility to damage due to stains, water exposure, and their associated undesirable effects such as physical damage, including wear, and odors.

The inventive liquid phase LCPs that are applied to a surface render the surface resistant to water and stains, and further protect it against the damaging effects of ultraviolet (UV) radiation. Thus, treatment with liquid phase LCPs is contemplated for fabrics, carpets, and other porous materials. Providing a liquid phase LCP having an Order Parameter $\geq 0.97$ would further provide surface sterilization of these surfaces and additionally eliminate unpleasant odors.

As previously demonstrated, testing of the inventive liquid phase LCPs demonstrated no bacterial uptake. They are thus likely not taken up by other living organisms, rendering them capable of use in, e.g., medical and food service applications.

Protection from Ultraviolet Light

Ultraviolet (UV) radiation reaching the earth's surface can be divided into UV-B radiation, which absorbs at 290–320 nm, and UV-A radiation, which absorbs at 320–400 nm. UV-A radiation can be further divided into UV-AI or far UV-A, which absorbs at 340–400 nm, and UV-An or near UV-A, which absorbs are 320–340 nm. Theoretical calculations and considerations, such as results obtained with candidate liquid phase LCPs using the SPARTAN software, previously described, indicate that a thin film coating of liquid phase LCPs to a surface will protect the surface against the damaging effects of UV radiation, both UV-B and UV-A.

In one embodiment, liquid phase LCPs as UV protectants were prepared to result in an Order Parameter in the range between about 0.2 to about 0.99, that is, polyiminoborane (PIB)$[BNH_2]_n$, polyaminoborane (PAB)$[BNH_4]_n$, and/or borozine polymers $[B_3N_3H_6]_n$ were modified to provide an Order Parameter in the range between 0.2 to 0.99. Compositions that resulted in these Order Parameters are those of the structure previously described where n is in the range between about 5 and about 100.

The above-described structural and functional aspects of the inventive liquid phase LCPs may be summarized as followed:

| Application | value of n | value of S |
|---|---|---|
| rinsing | 20–100 | 0.2–0.99 |
| lubricant/coolant | 1–10 | 0.2–0.99 |
| sterilantprotectant | 100–130 | 0.97–0.99 |
| non-sterilant protectant | 5–100 | 0.2–0.99 |

Other Applications

Many currently available cosmetics contain silicones, which are compounds of silica and carbon, as ingredients. In cosmetic manufacture and formulation processes, silica and silica oxides are by-products that eventually enter landfills., and pipes are installed in the landfills to remove biogases that result from the breakdown of these ingredients. Over time, these by-products are anaerobically reduced to various silica-oxygen solids, which accumulate in and eventually plug the pipes.

The inventive liquid phase LCPs, however, are resistant to breakdown under the anaerobic conditions typically encountered in landfills. In addition, because they form a layer of polymer chains that are nearly aligned, the liquid phase LCPs form a protective barrier against attack by oxygen radicals such as hydroxyl radicals ($OH^-$), ozone ($O_3$), and UV light. In addition, the liquid phase LCPs are water insoluble, physiologically inert, and not absorbed by living cells, thus they are desirable for use as a base in a wide range of cosmetics, such as sun screens, foundations, moisturizers, creams, lotions, colorants, gels, sprays, etc.

Other variations or embodiments of the invention will also be apparent to those of ordinary skill in the art from the above figures, description, and examples. For example, a mixture of two or more liquid phase LCPs having different average Order Parameters and/or different n values, may be prepared and used for combined applications. The specific compositions and percentage volumes of each in the mixture may be tailored to the application desired. As only one example, liquid phase LCPs having the structure previously described may be prepared to result in a mixture having 50% liquid phase LCPs having an average Order Parameter $\geq 0.97$ for surface sterilizing processes, and 50% liquid phase LCPs having an average Order Parameter in the range of about 0.5 to about 0.8 for rinsing processes. This mixture could be used, for example, for processing and surface sterilizing metal or ceramic parts. Thus, the forgoing embodiments are not to be construed as limiting the scope of this invention.

What is claimed is:

1. A liquid phase liquid crystal polymer (LCP) compound comprising a polyiminoborane $[BNH_2]_x$, polyaminoborane $[BNH_4]_x$, and/or borozine polymer $[B_3N_3H_6]_x$ backbone and at least one silicon and/or phosphorous side chain linked to the backbone, the compound exhibiting an average Order Parameter (S) in the range between about 0.2 to about 0.99 calculated by $S=\frac{1}{3}[3\cos^2\theta-1]$, where $\theta$ is the angle between the axis of a liquid phase LCP molecule and the vertical direction, and where x is in a range of about 10 to about 90.

2. A liquid phase liquid crystal polymer (LCP) comprising a compound selected from the group consisting of (—BH—NR—BH—NR'—)$_x$, (—BH$_2$—NHR—BH—HNR'—)$_x$,

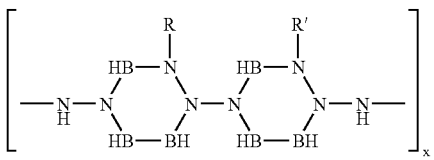

and combinations thereof, where x in the range of about 10 to about 90, R and R' are (CH$_3$)$_3$SiO[SiO(CH$_3$)$_2$]$_n$Si(CH$_3$)$_3$ and n is in the range of 1 to 130.

3. A rinse, lubricant, coolant, and/or protectant process for a part comprising treating the part with a liquid phase liquid crystal polymer (LCP) comprising a backbone chain of compounds selected from the group consisting of [BNH$_2$]$_x$, [BNH$_4$]$_x$, [B$_3$N$_3$H$_6$]$_x$, and combinations thereof, and at least one side chain comprising a compound selected from the group consisting of silicon, phosphorous, and combinations thereof linked to the backbone to form (—BH—NR—BH—NR'—)$_x$ (abbreviated as PIB), (—BW—NHR—BH—HNR'—)$_x$ (abbreviated as PAB), and/or

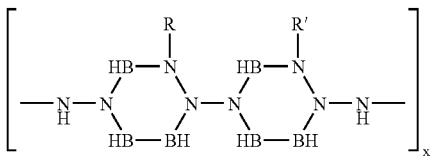

(abbreviated as PBZ), where R and R' are (CH$_3$)$_3$SiO[SiO(CH$_3$)$_2$]$_n$Si(CH$_3$)$_3$, x is in the range of about 10 to about 90, and n is in the range of 20–100 for rinse processes, n is in the range of 1–10 for lubricant/cooling processes, n is in the range of 100–130 for surface sterilization processes, and n is in the range of 5–100 for protectant processes.

4. A method for rinsing process chemicals from an apparatus comprising
contacting the processed apparatus under conditions sufficient to reduce the process chemical from the apparatus with a liquid phase liquid crystal polymer (LCP) having molecules of a polyiminoborane [BNH$_2$]$_x$, polyaminoborane [BNH$_4$]$_x$, and/or borozine polymer [B$_3$N$_3$H$_6$]$_x$ backbone, and at least one silicon and/or phosphorous side chain linked to the backbone to form (—BH—NR—BH—NR'—)$_x$ (abbreviated as PIB), (—BH$_2$—NHR—BH—HNR'—)$_x$ (abbreviated as PAB), and/or

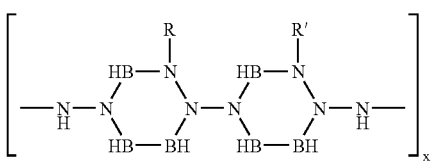

(abbreviated as PBZ), where R and R' are (CH$_3$)$_3$SiO[SiO(CH$_3$)$_2$]$_n$Si(CH$_3$, x is in the range of about 10 to about 90, and n is in the range of 20–100 for rinse processes, n is in the range of 1–10 for lubricant/cooling processes, n is in the range of 100–130 for surface sterilization processes, and n is in the range of 5–100 for protectant processes, to result in an average Order Parameter (S) in the range of about 0.2 to about 0.99 calculated by S=⅓ [3 cos$^2$ θ–1], where θ is the angle between the axis of a liquid phase LCP molecule and the vertical direction.

5. The method of claim 4 wherein the average Order Parameter is in the range of about 0.5 to about 0.8.

6. A method for lubricating and/or cooling machined parts comprising
contacting the part under conditions sufficient to lubricate and/or cool the part with a liquid phase liquid crystal polymer (LCP) having a polyiminoborane [BNH$_2$]$_x$, polyaminoborane [BNH$_4$]$_x$, and/or borozine polymer [B$_3$N$_3$H$_6$]$_x$ backbone, and at least one silicon and/or phosphorous side chain linked to the backbone to yield an average Order Parameter (S) in the range between about 0.2 to about 0.99 calculated by S=⅓ [3 cos$^2$ θ–1], where θ is the angle between the axis of a liquid phase LCP molecule and the vertical direction, and where x is in a range of about 10 to about 90.

7. The method of claim 5 wherein the part is selected from the group consisting of a metal part, a ceramic part, and combinations thereof.

8. An engine fluid comprising a liquid phase liquid crystal polymer (LCP) having a polyiminoborane [BNH$_2$]$_x$, polyaminoborane [BNH$_4$]$_x$, and/or borozine polymer [B$_3$N$_3$H$_6$]$_x$ backbone, and at least one silicon and/or phosphorous side chain linked to the backbone to yield an average Order Parameter in the range between about 0.2 to about 0.99 calculated by S=⅓ [3 cos$^2$ θ–1], where θ is the angle between the axis of a liquid phase LCP molecule and the vertical direction, and where x is in a range of about 10 to about 90.

9. The engine fluid of claim 8 selected from the group consisting of a motor oil, a transmission fluid, a brake fluid, a power steering fluid, a hydraulic fluid, and combinations thereof.

10. A method for sterilizing a surface comprising contacting the surface under conditions sufficient to coat the surface with a liquid phase liquid crystal polymer (LCP) film having a polyiminoborane [BNH$_2$]$_x$, polyaminoborane [BNH$_4$]$_x$, and/or borozine [B$_3$N$_3$H$_6$]$_x$ backbone, and at least one silicon and/or phosphorous side chain linked to the backbone to yield an average Order Parameter (S) in the range between about 0.2 to about 0.99 calculated by S=⅓ [3 cos$^2$ θ–1], where θ is the angle between the axis of a liquid phase LCP molecule and the vertical direction, and where x is in a range of about 10 to about 90.

11. A method for protecting a surface comprising contacting the surface under conditions sufficient to coat the surface with a liquid phase liquid crystal polymer (LCP) film having a polyiminoborane [BNH$_2$]$_x$, polyaminoborane [BNH$_4$]$_x$, and/or borozine [B$_3$N$_3$H$_6$]$_x$ backbone, and at least one silicon and/or phosphorous side chain linked to the backbone to yield an average Order Parameter (S) in the range between about 0.2 to about 0.99 calculated by S=⅓ [3 cos$^2$ θ–1], where θ is the angle between the axis of a liquid phase LCP molecule and the vertical direction, and where x is in a range of about 10 to about 90.

12. The method of claim 11 wherein the liquid phase LCP protects against a hazard selected from the group consisting of dehydration, moisture, microorganisms, macroorganisms, ultraviolet light, and combinations thereof.

13. A method for selecting a liquid phase liquid crystal polymer (LCP) for an indicated use comprising providing a liquid phase LCP comprising molecules of a polyiminoborane $[BNH_2]_x$, polyaminoborane $[BNH_4]_x$, and/or borozine $[B_3N_3H_6]_x$ backbone, and adding to the backbone at least one side chain containing molecules selected from the group consisting of silicon, phosphorous, and combinations thereof, to result in the liquid phase LCP having a desired average Order Parameter less than a solid phase and calculated by $S=\frac{1}{3}[3\cos^2\theta-1]$, where $\theta$ is the angle between the axis of a liquid phase LCP molecule and the vertical direction, and where x is in a range of about 10 to about 90.

14. The method of claim 13 further comprising thereafter using the resulting liquid phase LCP for the indicated use selected from the group consisting of a rinsing agent, a lubricant/coolant, a protectant, and combinations thereof.

15. The method of claim 13 wherein the liquid phase LCP is used as a rinsing agent with an average Order Parameter in the range of about 0.2 to about 0.99.

16. The method of claim 13 wherein the liquid phase LCP is used as a lubricant/coolant with an average Order Parameter in the range of 0.2 to about 0.99.

17. The method of claim 13 wherein the liquid phase LCP is used as a protectant to sterilize a surface with an average Order Parameter in the range of about 0.97 to about 0.99.

18. The method of claim 13 wherein the liquid phase LCP is used as a surface protectant with an average Order Parameter in the range of about 0.2 to about 0.99.

19. The method of claim 15, the average Order Parameter in the range of about 0.5 to about 0.8.

* * * * *